United States Patent
Zhu et al.

(10) Patent No.: US 7,807,213 B2
(45) Date of Patent: **\*Oct. 5, 2010**

(54) METHOD AND SYSTEM FOR CHARACTERIZING POROUS MATERIALS

(75) Inventors: Jianhong Zhu, Austin, TX (US); Dorel Ioan Toma, Dripping Springs, TX (US)

(73) Assignee: Tokyo Electron Limited, Tokyo (JP)

( * ) Notice: Subject to any disclaimer, the term of this patent is extended or adjusted under 35 U.S.C. 154(b) by 501 days.

This patent is subject to a terminal disclaimer.

(21) Appl. No.: 11/689,937

(22) Filed: Mar. 22, 2007

(65) Prior Publication Data

US 2007/0190232 A1 Aug. 16, 2007

Related U.S. Application Data

(63) Continuation of application No. 10/902,578, filed on Jul. 30, 2004, now Pat. No. 7,238,382.

(51) Int. Cl.
*G01N 13/00* (2006.01)
*B01D 59/12* (2006.01)
*C23C 16/52* (2006.01)

(52) U.S. Cl. .................. 427/8; 374/4; 95/45; 95/51

(58) Field of Classification Search .................. 427/8; 347/4; 95/51
See application file for complete search history.

(56) References Cited

U.S. PATENT DOCUMENTS

| | | | |
|---|---|---|---|
| 6,211,561 B1 * | 4/2001 | Zhao | 257/522 |
| 6,500,770 B1 * | 12/2002 | Cheng et al. | 438/782 |
| 6,769,288 B2 * | 8/2004 | Ward et al. | 73/40.7 |
| 2003/0007543 A1 * | 1/2003 | Grenfell et al. | 374/57 |
| 2003/0143839 A1 * | 7/2003 | Raaijmakers et al. | 438/633 |

OTHER PUBLICATIONS

Wente, John, Patching Bicycle Tubes (online), Apr. 2003 (retired on Nov. 28, 2006) retrieved from the internet: <URL:http//www.oklahomabicyclesociety.com/hinttips/patching/htm>.

Brown, Sheldon, Bicycles Tires and Tubes (online), Jun. 2002 (retrieved on Nov. 28, 2006); retrieved from the internet: <URL:http//www.sheldonbrown.com/tires/html> pp. 2-4.

"Locating water leaks in recreational vehicles" (online), Jun. 2002 (retrieved on Nov. 28, 2006); retrieved from internet: <URL:http//www.rvleaks.com/How.htm>.

Troubleshooting Guide (online), Jun. 2002 (retrieved Nov. 28, 2006) retrieved from internet <URL:http//parkaway.com/ts.htm>.

* cited by examiner

*Primary Examiner*—Timothy H Meeks
*Assistant Examiner*—Cachet I Sellman
(74) *Attorney, Agent, or Firm*—Oblon, Spivak, McClelland, Maier & Neustadt, L.L.P.

(57) ABSTRACT

A method and system for diagnosing the effectiveness of a treatment on a porous material. For example, the porous material can include a porous low dielectric constant material. In particular, the method can utilize FTIR spectroscopy to characterize the porosity of materials, and assess the effectiveness of sealing pores in the material.

21 Claims, 8 Drawing Sheets

METHOD AND SYSTEM FOR CHARACTERIZING POROUS MATERIALS

CROSS-REFERENCE TO RELATED APPLICATIONS

This application is a Continuation of and claims the benefit of priority under 35 U.S.C. §120 from U.S. Ser. No. 10/902,578, now U.S. Pat. No. 7,238,382, filed Jul. 30, 2004, the entire contents of which is incorporated herein by reference.

BACKGROUND OF THE INVENTION

1. Field of the Invention

The present invention relates to a method and system for characterizing porous materials and, more particularly, to a method and system for characterizing the porosity of porous materials and the effectiveness of treating porous materials.

2. Description of Related Art

As is known to those in the semiconductor art, interconnect delay is a major limiting factor in the drive to improve the speed and performance of integrated circuits (IC). One way to minimize interconnect delay is to reduce interconnect capacitance by using low dielectric constant (low-k) materials during production of the IC. Thus, in recent years, low-k materials have been developed to replace relatively high dielectric constant insulating materials, such as silicon dioxide. In particular, low-k films are being utilized for inter-level and intra-level dielectric layers between metal layers of semiconductor devices. Additionally, in order to further reduce the dielectric constant of insulating materials, material films are formed with pores, i.e., porous low-k dielectric films. Such low-k films can be deposited by a spin-on dielectric (SOD) method similar to the application of photo-resist, or by chemical vapor deposition (CVD). Thus, the use of low-k materials is readily adaptable to existing semiconductor manufacturing processes.

While low-k materials are promising for fabrication of semiconductor circuits, the present inventors have recognized that these films also provide many challenges. First, low-k films tend to be less robust than more traditional dielectric layers and can be damaged during wafer processing, such as by plasma etching and plasma ashing processes generally used in patterning the dielectric layer. Further, some low-k films tend to be highly reactive when damaged, particularly after patterning, thereby allowing the low-k material to absorb water and/or react with other vapors and/or process contaminants that can alter the electrical properties of the dielectric layer. For example, following pattern etching, the exposed surfaces can change from being hydrophobic to becoming hydrophilic, the exposed surface layer can become depleted of carbon (C), and the pores can retain contaminants from the etch process.

Moreover, the present inventors have recognized that the porosity of some low-k dielectric films often exacerbates the problems of integrating metallization with the dielectric. In general, the integration of copper metallization with low-k dielectric films requires the use of a damascene structure, wherein metal wiring patterns are formed within the dielectric film prior to copper deposition. In order to minimize the diffusion of copper into the dielectric film, a barrier layer is typically formed on the internal surfaces of these patterns following pattern etching.

However, exposure of the pores and/or damage of the low-k film following the etching of patterns in the dielectric film causes problems with diffusion of the precursors of the barrier material and copper through imperfections in the barrier film local to these exposed pores, as well as poor adhesion of the barrier layer to the dielectric film.

SUMMARY OF THE INVENTION

One object of the invention is to reduce or eliminate any of the above-described problems or other problems in the prior art relating to processing porous films.

Another object of the invention is to determine the effectiveness of treating a porous material.

Another object of the invention is to determine the effectiveness of sealing a porous material.

Yet another object of the invention is to determine the effectiveness of sealing a porous low dielectric constant film.

Still another object of the invention is to determine the effectiveness of treating a porous film in order to reduce diffusion of barrier material, seed material, or bulk material, or a combination thereof into the porous film and/or determine the effectiveness of improving adhesion of the barrier film to the porous film.

Yet another object of the invention is to characterize the porosity of a porous material.

These and other objects of the invention may be accomplished by a method of characterizing a porous material. According to one aspect of the invention, the method includes performing a sealing process on one or more surfaces of a porous material formed on a substrate; exposing the one or more surfaces on the porous material to a treating agent, wherein the treating agent is configured to permeate through the one or more surfaces and disperse within the porous material; and monitoring a release of the treating agent from the porous material following the exposure.

According to another aspect of the invention, a porous material includes a bulk material having a matrix of pores; a sealing layer coupled to the bulk material, wherein the sealing layer is configured to be substantially devoid of pores; and a treating agent configured to permeate the sealing layer and disperse within the matrix of pores.

According to yet another aspect of the invention, a system for characterizing a porous material includes a sealing system configured to form a sealing layer on one or more surfaces of the porous material; a treating system coupled to the sealing system, and configured to expose the porous material to a treating agent, wherein the treating agent is configured to permeate through the sealing layer and disperse within a matrix of pores in the porous material; and a monitoring system coupled to the treating system, and configured to monitor a release of the treating agent from the porous material.

DETAILED DESCRIPTION OF EXEMPLARY EMBODIMENTS

Figure 1A:
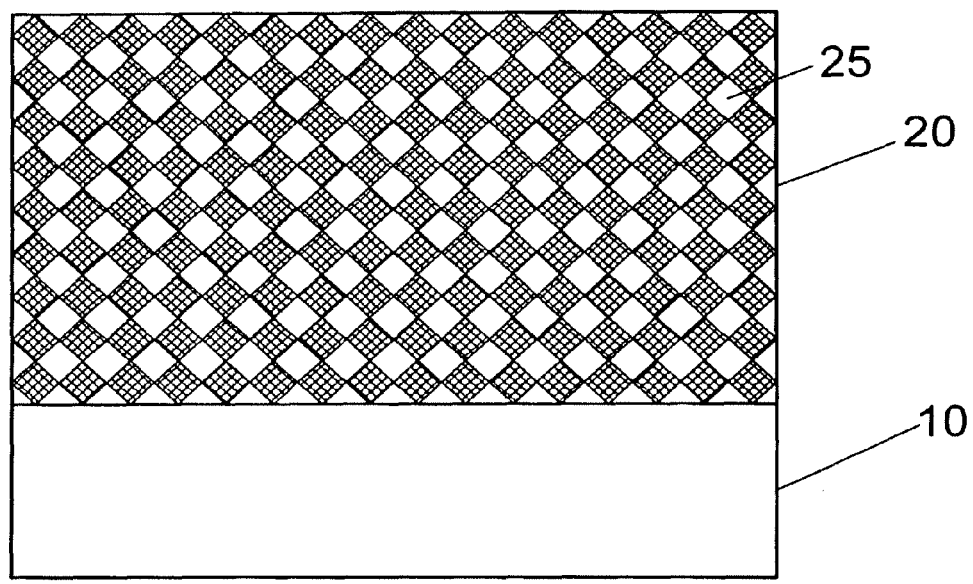
FIGS. 1A through 1D present a simplified schematic representation of a method of characterizing a porous film in accordance with an embodiment of the invention.

In the following description, to facilitate a thorough understanding of the invention and for purposes of explanation and not limitation, specific details are set forth, such as a particular process for characterizing porous films or porous substrates, and various descriptions of the porous films and porous substrates. However, it should be understood that the invention may be practiced with other embodiments that depart from these specific details.

Nonetheless, it should be appreciated that, contained within the description are features which, notwithstanding the inventive nature of the general concepts being explained, are also of an inventive nature.

As described in the Background of the Invention section above, porous films such as low-k dielectric films are susceptible to damage and contamination, and can cause barrier metal diffusion and poor adhesion. The present inventors have discovered that performing a sealing treatment can reduce or eliminate some of these problems. Moreover, as will be further described below, the present inventors have recognized that it would be useful to determine the effectiveness of the sealing formed on the porous film and/or a characteristic of the porous film. Thus, referring now to the drawings, wherein like reference numerals designate identical or corresponding parts throughout the several views, FIGS. 1A through 1D depict a schematic representation of a substrate having a porous material formed thereon and undergoing a method for characterizing the porous material according to an embodiment of the present invention. Additionally, FIG. 2 presents a flow chart 100 of performing the method steps corresponding to FIGS. 1A through 1D. Although in FIGS. 1A through 1D, the porous material is described as a porous film formed on a substrate, the invention is applicable to a porous substrate.

Figure 2:
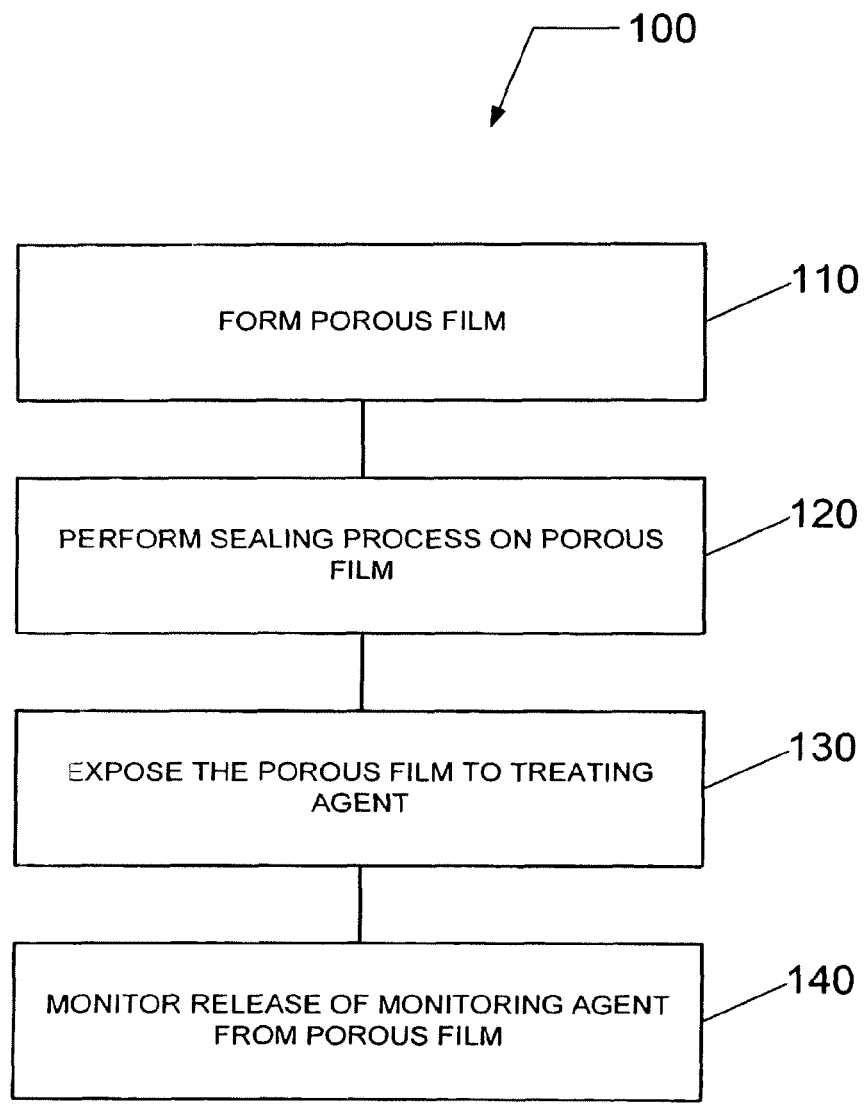
FIG. 2 presents a method of characterizing a porous film according to an embodiment of the present invention.

As shown in FIG. 1A, and step 110 of FIG. 2, a porous film 20, having a matrix of pores 25, is formed on an upper surface of a substrate 10 that may or may not include additional layers. The substrate 10 may be a semiconductor, or any other substrate to which the dielectric film is to be formed upon. For example, the porous film 20 can include a low dielectric constant (low-k) dielectric film that has a nominal dielectric constant value less than the dielectric constant of $SiO_2$, which is approximately 4 (e.g., the dielectric constant for thermal silicon dioxide can range from 3.8 to 3.9). More specifically, the porous film 20 may have a dielectric constant of less than 3.0, or a dielectric constant ranging from 1.6 to 2.7.

Additionally, for example, the porous film 20 can be formed using chemical vapor deposition (CVD) techniques, or spin-on dielectric (SOD) techniques such as those offered in the Clean Track ACT 8 SOD and ACT 12 SOD coating systems commercially available from Tokyo Electron Limited (TEL). The Clean Track ACT 8 (200 mm) and ACT 12 (300 mm) coating systems provide coat, bake, and cure tools for SOD materials. The track system can be configured for processing substrate sizes of 100 mm, 200 mm, 300 mm, and greater. Other systems and methods for forming a dielectric film on a substrate are well known to those skilled in the art of both spin-on dielectric technology and CVD dielectric technology.

Moreover, the porous film 20 may include at least one of an organic, inorganic, and inorganic-organic hybrid material. For example, the porous film may include an inorganic, silicate-based material, such as oxidized organosilane (or organo siloxane), deposited using CVD techniques. Examples of such films include Black Diamond™ CVD organosilicate glass (OSG) films commercially available from Applied Materials, Inc., or Coral™ CVD films commercially available from Novellus Systems. Additionally, for example, porous dielectric films can include single-phase materials, such as a silicon oxide-based matrix having $CH_3$ bonds that are broken during a curing process to create small voids (or pores). Additionally, for example, porous dielectric films can include dual-phase materials, such as a silicon oxide-based matrix having pores of organic material (e.g., porogen) that is evaporated during a curing process. Alternatively, the porous film 20 may include an inorganic, silicate-based material, such as hydrogen silsesquioxane (HSQ) or methyl silsesquioxane (MSQ), deposited using SOD techniques. Examples of such films include FOx HSQ commercially available from Dow Corning, XLK porous HSQ commercially available from Dow Corning, and JSR LKD-5109 commercially available from JSR Microelectronics. Still alternatively, the porous film 20 can include an organic material deposited using SOD techniques. Examples of such films include SiLK-I, SiLK-J, SiLK-H, SiLK-D, and porous SiLK semiconductor dielectric resins commercially available from Dow Chemical, and FLARE™, and Nano-glass commercially available from Honeywell. Additionally, for example, porous dielectric films can include Aurora™ low-k materials, commercially available from ASM America, Inc. Additionally, for example, porous dielectric films can include Orion™ low-k materials, commercially available from Trikon Technologies. Additionally, for example, porous dielectric films can include Zirkon™ low-k materials, commercially available from Rohm and Haas Electronic Materials. Additionally, for example, porous dielectric films can include nano-clustering silica, commercially available from Catalysis and Chemicals Industry Company, Limited.

Figure 1B:
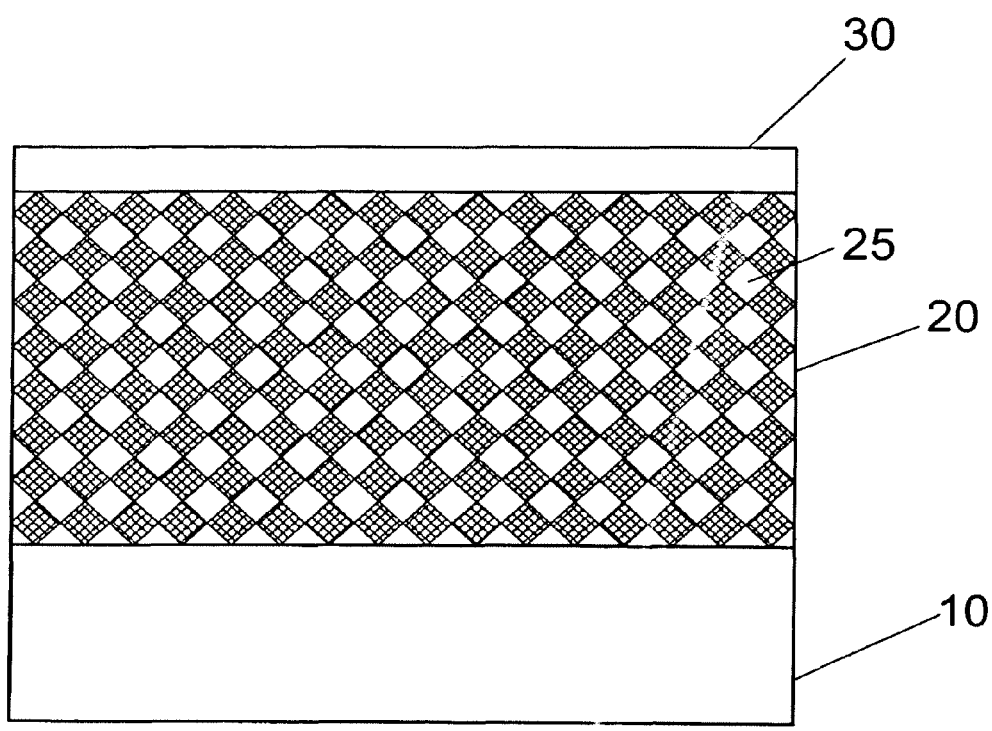

Once the porous film 20 is prepared, an exposed surface of the porous film 20 is treated using a sealing process in step 120 in order to seal exposed pores at this surface and form a sealing layer 30 as shown in FIG. 1B. As discussed in the Background of the Invention section above, the present inventor has recognized that exposed pores in the porous film can be sites for contamination, as well as sites for the accumulation of moisture. For instance, the exposure of pores in a porous low-k dielectric film following pattern etching of the porous film can lead to loss of the dielectric constant (i.e., increase in the value of the dielectric constant), moisture contamination, and accumulation of post-etch residue. Additionally, for example, exposed pores in a patterned porous low-k dielectric film are susceptible to poor barrier film quality in back end of line (BEOL) metal interconnects and intra-connects that leads to metal migration into the low-k dielectric film. Therefore, porous films should be sealed to prevent contamination therein, and provide good barrier properties for subsequent processing.

The sealing process can include any sealing process configured to substantially close off the exposed pores, thus sealing the exposed surface to form the sealing layer. For example, the sealing process for a porous low-k dielectric film can include a plasma treatment, whereby a surface of the porous film undergoes densification to form sealing layer 30 through exposure to plasma. The plasma treatment can include a dry plasma etching process to transfer a pattern to the porous film, or it can include a dry plasma ashing step to remove photoresist or photoresist residue from the porous film, or it may include plasma immersion ion bombardment of the porous film surface layer. Additionally, for example, the sealing process can include densification of a porous film surface layer using ion implantation, as described in detail by pending U.S. patent application Ser. No. 10/857,935, filed on Jun. 2, 2004, entitled "METHOD AND SYSTEM FOR USING ION IMPLANTATION FOR TREATING A LOW-K DIELECTRIC FILM", the entire content of which is incorporated by reference in its entirety. Additionally, for example, the sealing process can include the exposure of the porous film to a sealing agent using liquid immersion treatment, vapor phase treatment, or supercritical fluid treatment. Details of sealing the porous films are provided in the pending U.S. patent application Ser. No. 10/682,196, filed on Oct. 10, 2003, entitled "METHOD AND SYSTEM FOR TREATING A DIELECTRIC FILM", the entire content of which is incorporated by reference. Additionally, for example, the sealing process can include the deposition of a thin film on the porous film in order to act as a sealing layer, or barrier layer. The thin film can be deposited using conventional techniques, such as spin-on techniques, and chemical vapor deposition (CVD).

In addition to treating the porous film by, for example sealing, the present inventor has further recognized that it is useful to determine the effectiveness of the treatment to the porous film. For example, different low-K films may require different treatment processes to provide the desired properties. Moreover, a particular low-K film may require different treatment techniques or levels of treatment depending on the processing steps that the film will be exposed to. Thus, the present inventor has discovered a method of determining the effectiveness of a seal formed on the porous film. By this inventive method, sealing techniques and the porous films themselves can be characterized.

Figure 1C:
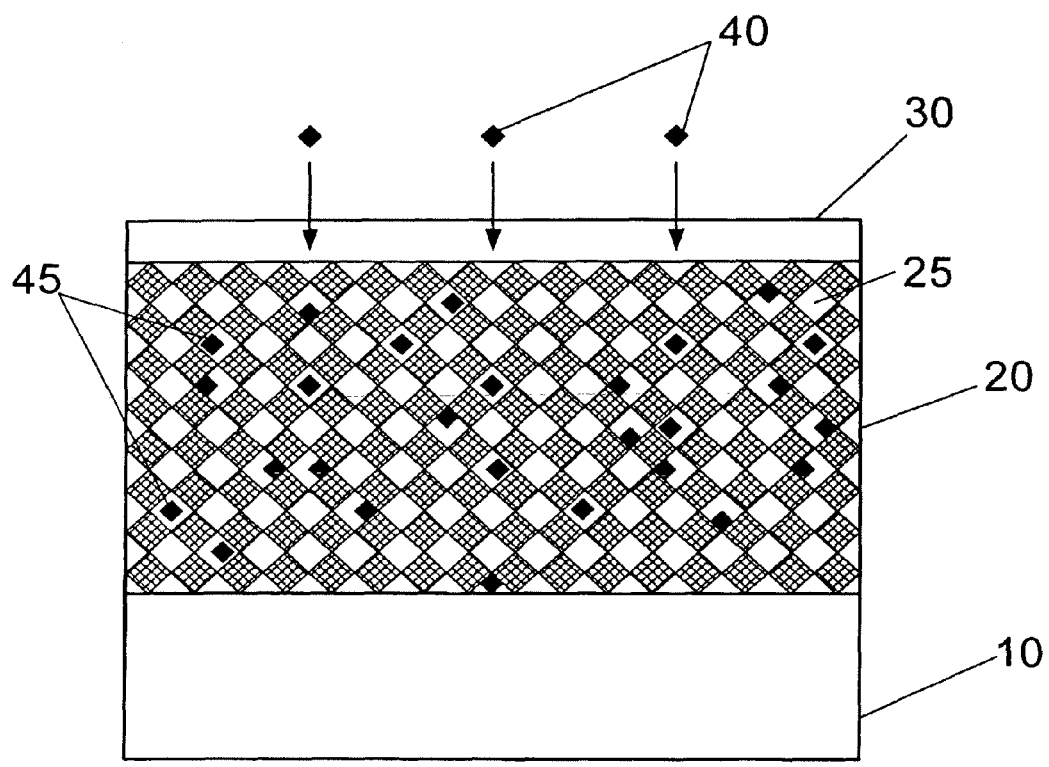
Figure 1D:
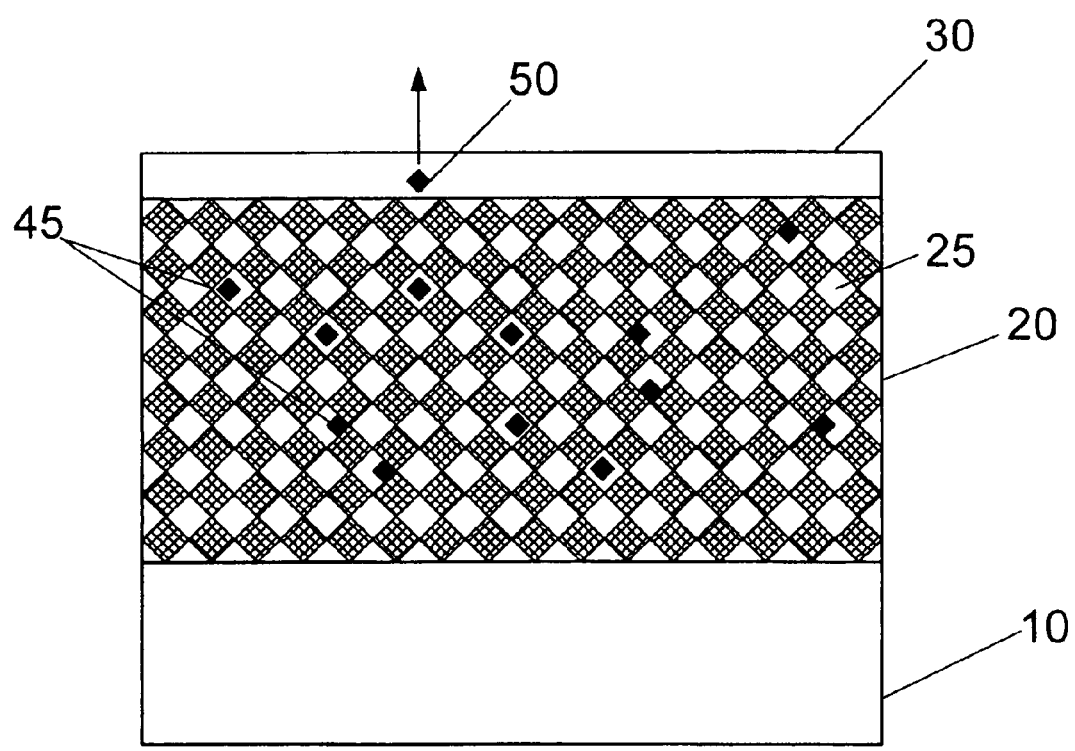

Referring now to FIG. 1C, the effectiveness of the sealing process is determined by exposing the porous film 20 and sealing layer 30 in step 130 to a treating agent. For example the treating agent can be prepared in a supercritical state. Additionally, for example, the treating agent can include supercritical carbon dioxide ($CO_2$). As shown in FIG. 1C, the treating agent 40 permeates through the sealing layer 30, and a fraction of the treating agent 45 disperses within the matrix of pores 25 in the porous film 20. The treating agent can include any atom or molecule capable of permeating through the sealing layer 30, and entering the porous film 20. Additionally, the treating agent can have a molecular size sufficiently small that permits the molecule to permeate through the sealing layer 30, and to enter the porous film 20. The exposure of the porous film 20 to the treating agent can take place during, or after the sealing process. For example, the sealing process can include use of a supercritical fluid to carry a sealing agent, whereby the sealing agent seals the porous film, and molecules of the supercritical fluid disperse within the porous film 20. Additionally, for example, the exposure of the porous film 20 to a treating agent can take place during, or after a supercritical fluid treating, cleaning, or healing process.

Following the exposure of the porous film 20 to the treating agent, the porous film 20 is monitored in step 140 using a treating agent monitoring system in order to detect the release of the treating agent from the matrix of pores through the sealing layer. The rate at which the treating agent is released from the porous film can be utilized to determine the effectiveness of the sealing process. For example, the treating agent monitoring system can include a Fourier Transform Infrared (FTIR) Spectrometer.

Figure 3:
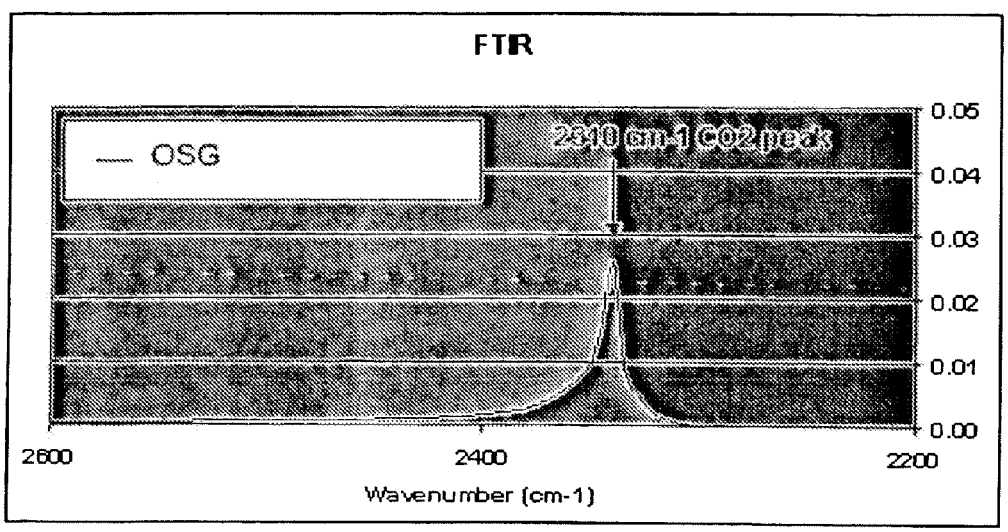
FIG. 3 illustrates an exemplary wavenumber spectrum obtained from characterizing a porous film.

In one example, a porous low-k film is exposed to supercritical $CO_2$, and a FTIR spectrometer is utilized to detect the release of $CO_2$ from the porous film. FIG. 3 illustrates an exemplary wavenumber spectrum for a porous organo-silica glass (OSG) film, such as a low-k Black Diamond® film. By inspection, the presence of $CO_2$ is detected by the existence of a $CO_2$ peak at 2340 $cm^{-1}$. As the $CO_2$ is released from the matrix of pores in the porous film, the wavenumber spectrum exhibits this peak. However, while time passes, this peak decays to a non-detectable level as substantially all of the $CO_2$ is released from the porous film. The amount of time it takes for the peak to decay is representative of the effectiveness of the sealing process. For example, where the peak decay occurs over a relatively long period of time, the sealing is determined to be effective. However, where the peak decay occurs over a very short period of time, the sealing is determined to be less effective. In one embodiment the effectiveness of the seal is determined by comparing a measured rate of release of the treating agent to a threshold value that indicates an effectively sealed film. As would be understood by one of ordinary skill in the art, determination of the effectiveness of a seal is in accordance with the present invention is largely dependent on the low-k film used and the process steps that the low-k film will be exposed to. In addition, to determining effectiveness, following the sealing process, the magnitude of the $CO_2$ peak in the wavenumber spectrum can be indicative of the capacity of the porous film to retain $CO_2$ within its matrix of pores and, hence, this magnitude may be useful for determining the pore size, pore volume, or combination thereof.

In a comparative example, two porous low-k films are prepared, the first of which is an OSG film, and the second of which is a methyl silsesquioxane (MSQ) film, such as a JSR LKD 5109 film. Following the deposition of each film, the films undergo an etching and ashing process with the additional intent of sealing each film. Thereafter, the effectiveness of the sealing process, i.e., plasma treatment, is determined, firstly, using ellipsometric porosimetry (EP), and secondly, using the method described above whereby the porous film is exposed to a treating agent and monitored using a FTIR spectrometer for release of the treating agent. Ellipsometric porosimetry involves exposing the porous film to vapor phase toluene, and monitoring the refractive index (RI) of the porous film while toluene is potentially adsorbed, and desorbed following the exposure to toluene. If the surface of the porous film is sufficiently sealed, then toluene can not enter and adsorb within the porous film, and the refractive index of the porous film remains unchanged during adsorption (ads) and desorption (des). On the contrary, if the porous film is not sufficiently sealed, then toluene can enter and adsorb within the porous film, and the refractive index of the porous film varies. While the EP method is effective for determining if a film is sealed or not sealed, this method cannot be used to determine various levels of the effectiveness of the seal, or to characterize the porous film itself. Moreover, the use of toluene may be ineffective or undesirable for certain films.

Figures 4A, 4B:
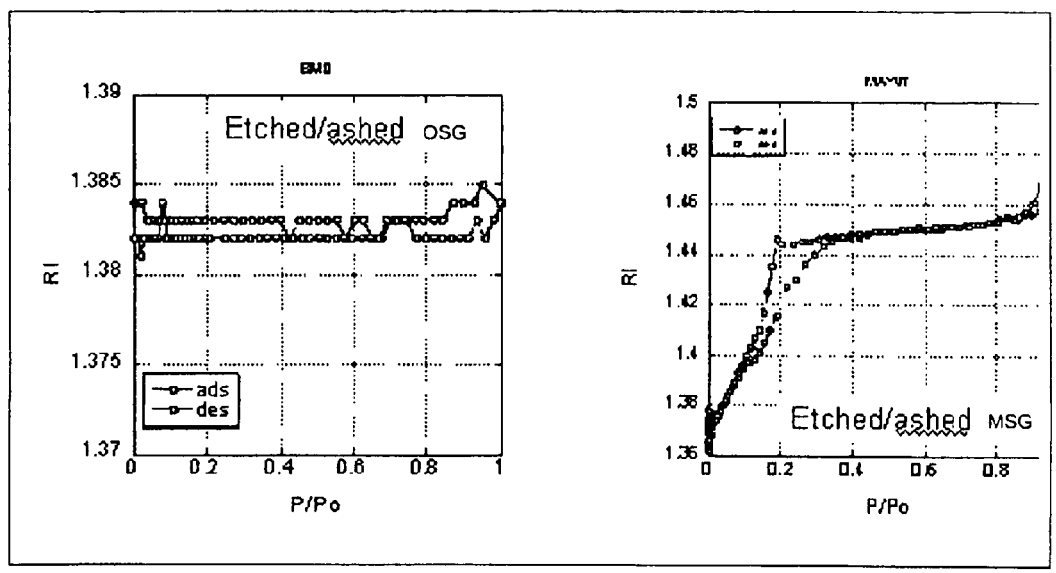
FIGS. 4A and 4B present exemplary data obtained from ellipsometric porosimetry measurements.

Table 1 presents the results of ellipsometric porosimetry measurements and FTIR $CO_2$ monitoring for both films as deposited, and following an etching/ashing process (or sealing process). For both films as deposited, EP results indicate open pores and, as expected, no $CO_2$ peak because both films have yet to be exposed to treating agent. Following the etching/ashing process, the EP results indicate the OSG film is sealed, and the MSQ film is not sealed. Specifically, FIG. 4A and FIG. 4B present the refractive index as a function of the pressure (P) of vapor phase toluene during exposure to the porous film (normalized by a reference pressure Po, such as a saturation pressure) for the OSG film and the MSQ film, respectively. Inspection of FIGS. 4A and 4B indicates that the OSG film is sealed (constant RI), and the MSQ film is not sealed (variable RI).

Furthermore, the exposure of both films to supercritical $CO_2$ and the FTIR monitoring of both films indicates that the OSG film exhibits a $CO_2$ peak immediately following the exposure to the treating agent and no detectable $CO_2$ peak five (5) hours after the exposure, while the MSQ film exhibits no detectable $CO_2$ peak immediately after the exposure or five hours after the exposure, which is consistent with the EP results. The complete absence of a peak for the MSQ film is believed to be due to the $CO_2$ escaping from the film faster than can be detected by the measurement techniques.

TABLE 1

|  | As-deposited | | Etched/ashed | | |
|  |  |  |  | FTIR CO2 peak | |
|  | EP | FTIR CO2 peak | EP | Right after | 5 hrs later |
| --- | --- | --- | --- | --- | --- |
| OSG | Open | No | Sealed | Yes | No |
| MSQ | Open | No | Open | No | No |

Figure 5:
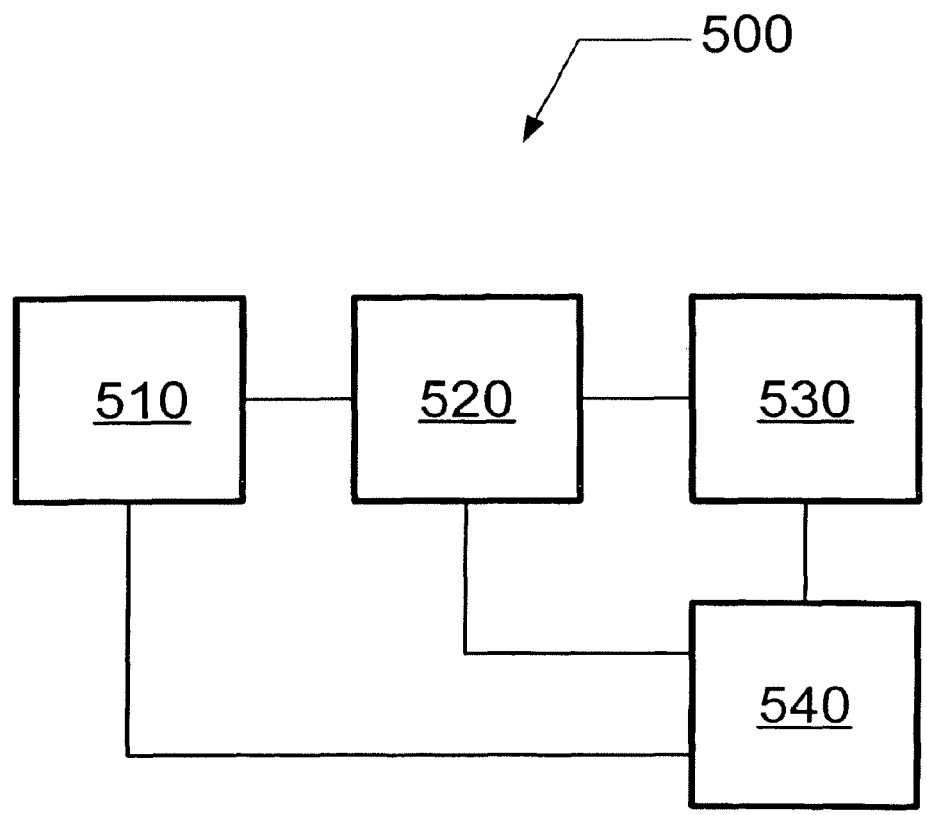
FIG. 5 presents a system for characterizing a porous film according to an embodiment of the invention.

Referring now to FIG. 5, a system for characterizing a porous film, or porous substrate, is described. The system 500 comprises a sealing system 510 configured to seal a porous film (or porous substrate), a treatment system coupled to the sealing system and configured to expose the porous film (or porous substrate) to a treating agent, and a treating agent monitoring system 530 coupled to the treatment system 520 and configured to monitor the release of the treating agent from the porous film (or porous substrate). The sealing system and the treatment system can be the same system. The sealing system can include a plasma treatment system, a dry plasma etching system, a dry plasma ashing system, a liquid immersion system, a vapor phase treatment system, a supercritical fluid processing system, an ion implantation system, or a deposition system (such as a spin-on deposition system, or a chemical vapor deposition system), or any combination thereof. The treatment system can include a supercritical fluid processing system, liquid immersion system, or vapor phase treatment system, or any combination thereof. The treating agent monitoring system can include a FTIR spectrometer, such as one commercially available from Thermo Nicolet, Model No. AVATAR 370 FT-IR.

Additionally, the system for characterizing porous films (or porous substrates) can include a controller 540 coupled to the sealing system 510, the treatment system 520, and the treating agent monitoring system 530. Controller 540 includes a microprocessor, memory, and a digital I/O port (potentially including D/A and/or A/D converters) capable of generating control voltages sufficient to communicate and activate inputs to the sealing system 510, treatment system 520, and treating agent monitoring system 530, as well as monitor outputs from these systems. A program stored in the memory is utilized to interact with the systems 510, 520, and 530 according to a stored process recipe. One example of controller 540 is a DELL PRECISION WORKSTATION 530™, available from Dell Corporation, Austin, Tex. The controller 540 may also be implemented as a general purpose computer, digital signal processor, etc.

Controller 540 may be locally located relative to the sealing system 510, the treatment system 520, and the treating agent monitoring system 530, or it may be remotely located via an internet or intranet. Thus, controller 540 can exchange data with the sealing system 510, the treatment system 520, and the treating agent monitoring system 530 using at least one of a direct connection, an intranet, and the internet. Controller 540 may be coupled to an intranet at a customer site (i.e., a device maker, etc.), or coupled to an intranet at a vendor site (i.e., an equipment manufacturer). Furthermore, another computer (i.e., controller, server, etc.) can access controller 540 to exchange data via at least one of a direct connection, an intranet, and the internet.

The controller 540 can be further configured to determine an effectiveness of the sealing process performed on a porous film (or porous substrate) and, more particularly, determine the effectiveness of the sealing layer formed by the sealing process. For example, the rate at which the treating agent is released from the porous film can be compared with a threshold value. If the measured rate exceeds the threshold value, then the porous film can be determined to not be effectively sealed. If the rate does not exceed the threshold value, then the porous film can be determined to be effectively sealed. Alternatively, the controller can determine the sealing process effectiveness from a treating agent release duration. The longer the time duration for release of the treating agent, the more effective the sealing layer.

Although only certain exemplary embodiments of this invention have been described in detail above, those skilled in the art will readily appreciate that many modifications are possible in the exemplary embodiments without materially departing from the novel teachings and advantages of this invention. For example, while the discussion of porous films has included porous low-k films, the present invention is not limited to treating only such films, and may be implemented to treat any porous film. Accordingly, all such modifications are intended to be included within the scope of this invention.

What is claimed is:

1. A method of characterizing a material comprising:
performing a sealing process on a surface of a porous dielectric film;
exposing said sealed surface of said porous dielectric film to a treating agent, which permeates through said sealed surface and disperses within said porous dielectric film; and
monitoring a release of said treating agent dispersed within said porous dielectric film through said sealed surface of said porous dielectric film to determine an effectiveness of said sealing process.

2. The method of claim 1, wherein said porous dielectric film comprises a porous low dielectric constant (low-k) film.

3. The method of claim 1, wherein said sealing process includes exposing said surface of said porous dielectric film to a plasma treatment process, a dry plasma etching process, a dry plasma ashing process, a vapor phase treatment process, a liquid immersion process, a deposition process, or a supercritical fluid process, or a combination thereof.

4. The method of claim 1, wherein said treating agent comprises a supercritical fluid.

5. The method of claim 1, wherein said treating agent comprises supercritical carbon dioxide.

6. The method of claim 1, wherein said monitoring said release of said treating agent includes using a Fourier transform infrared (FTIR) spectrometer.

7. The method of claim 6, wherein said FTIR spectrometer is configured to detect a release of carbon dioxide from said porous dielectric film.

8. The method of claim 1, further comprising:
determining said effectiveness of said sealing process based on a rate at which said treating agent is released from said porous dielectric film.

9. The method of claim 8, wherein said determining said effectiveness includes comparing said rate to a threshold value, and wherein said rate does not exceed said threshold value indicates an effectively sealed porous dielectric film.

10. The method of claim 1, wherein the treating agent is liquid immersion treatment, vapor phase treatment, supercritical fluid, or any combination thereof.

11. The method of claim 1, wherein the treating agent has a molecular size which permits a molecule of the treating agent to permeate through the sealed surface and enter the porous dielectric film.

12. A method of characterizing a material comprising:
performing a sealing process on a surface of a porous dielectric film;
exposing said sealed surface of said porous dielectric film to a treating agent, wherein said treating agent is liquid immersion treatment, vapor phase treatment, supercritical fluid, or any combination thereof, said treating agent configured to permeate through said sealed surface and disperse within said porous dielectric film; and
monitoring a release of said treating agent dispersed within said porous dielectric film through said sealed surface of said porous dielectric film to determine an effectiveness of said sealing process.

13. The method of claim 12, wherein said porous dielectric film comprises a porous low dielectric constant (low-k) film.

14. The method of claim 12, wherein said sealing process includes exposing said surface of said porous dielectric film to a plasma treatment process, a dry plasma etching process, a dry plasma ashing process, a vapor phase treatment process, a liquid immersion process, a deposition process, or a supercritical fluid process, or a combination thereof.

15. The method of claim 12, wherein said exposing said treating agent comprises a supercritical fluid.

16. The method of claim 12, wherein said treating agent comprises supercritical carbon dioxide.

17. The method of claim 12, wherein said monitoring said release of said treating agent includes using a Fourier transform infrared (FTIR) spectrometer.

18. The method of claim 17, wherein said FTIR spectrometer is configured to detect a release of carbon dioxide from said porous dielectric film.

19. The method of claim 12, further comprising:
determining said effectiveness of said sealing process based on a rate at which said treating agent is released from said porous dielectric film.

20. The method of claim 19, wherein said determining said effectiveness includes comparing said rate to a threshold value, and wherein said rate does not exceed said threshold value indicates an effectively sealed porous dielectric film.

21. The method of claim 12, wherein said performing comprises performing a sealing process on a porous substrate.

* * * * *